United States Patent
Pijl et al.

(10) Patent No.: US 10,142,790 B2
(45) Date of Patent: Nov. 27, 2018

(54) CONSERVATION OF BATTERY LIFE IN GPS ACCESSING PORTABLE DEVICES

(71) Applicant: KONINKLIJKE PHILIPS N.V., Eindhoven (NL)

(72) Inventors: Marten Jeroen Pijl, Eindhoven (NL); Paul Michael Fulton, Cambridge (GB); Heribert Baldus, Aachen (DE)

(73) Assignee: KONINKLIJKE PHILIPS N.V., Eindhoven (NL)

(*) Notice: Subject to any disclaimer, the term of this patent is extended or adjusted under 35 U.S.C. 154(b) by 199 days.

(21) Appl. No.: 14/363,824

(22) PCT Filed: Dec. 19, 2012

(86) PCT No.: PCT/IB2012/057448
§ 371 (c)(1),
(2) Date: Jun. 9, 2014

(87) PCT Pub. No.: WO2013/093785
PCT Pub. Date: Jun. 27, 2013

(65) Prior Publication Data
US 2015/0087332 A1    Mar. 26, 2015

Related U.S. Application Data

(60) Provisional application No. 61/577,737, filed on Dec. 20, 2011.

(51) Int. Cl.
*H04W 4/02* (2018.01)
*A61B 5/11* (2006.01)
(Continued)

(52) U.S. Cl.
CPC .......... *H04W 4/027* (2013.01); *A61B 5/1118* (2013.01); *G01S 19/34* (2013.01); *G01S 19/49* (2013.01)

(58) Field of Classification Search
CPC ........ H04W 4/027; G01S 19/34; G01S 19/45; G01S 19/47; G01S 19/48; G01S 19/49
(Continued)

(56) References Cited

U.S. PATENT DOCUMENTS 7,702,370 B2    4/2010  Persico
8,362,949 B2 *  1/2013  Yang ................. G01S 19/34
                                                342/357.31
(Continued)

FOREIGN PATENT DOCUMENTS

EP    2372394       10/2011
JP    2000275596 A  10/2000
(Continued)

OTHER PUBLICATIONS

Leonhardi et al: "A Comparison of Protocols for Updating Location Information"; Cluster Computing 4. pp. 355-367, 2001.

*Primary Examiner* — Anthony Addy
*Assistant Examiner* — Donald H Braswell

(57) ABSTRACT

A method of controlling a device that includes a receiver and a movement sensor includes (a) deactivating the receiver; (b) while the receiver is deactivated, analyzing measurements from the movement sensor to determine a measure of the distance the device has moved from a first location; and (c) in the event that it is determined from the measurements from the movement sensor that the device has moved from the first location by more than a threshold distance, activating the receiver and using the receiver to obtain a second measurement of the location of the device.

9 Claims, 2 Drawing Sheets

(51) Int. Cl.
*G01S 19/34* (2010.01)
*G01S 19/49* (2010.01)

(58) Field of Classification Search
USPC .................................................. 455/456.1
See application file for complete search history.

(56) References Cited

U.S. PATENT DOCUMENTS

| | | | |
|---|---|---|---|
| 9,041,528 B2* | 5/2015 | Howard | A42B 3/046 340/5.61 |
| 2006/0119508 A1 | 6/2006 | Miller | |
| 2009/0098880 A1* | 4/2009 | Lindquist | G01S 19/34 455/456.1 |
| 2009/0132197 A1 | 5/2009 | Rubin et al. | |
| 2009/0278738 A1 | 11/2009 | Gopinath | |
| 2010/0057359 A1 | 3/2010 | Caballero et al. | |
| 2010/0127926 A1 | 5/2010 | Wang | |
| 2011/0029277 A1* | 2/2011 | Chowdhary | G01C 21/165 702/150 |
| 2011/0140956 A1 | 6/2011 | Henry et al. | |
| 2012/0206296 A1* | 8/2012 | Wan | A01K 11/008 342/357.31 |
| 2013/0079949 A1* | 3/2013 | Friend | B60W 40/076 701/1 |

FOREIGN PATENT DOCUMENTS

| | | |
|---|---|---|
| JP | 2007293632 A | 11/2007 |
| JP | 2011504578 A | 2/2011 |
| JP | 2011247845 A | 12/2011 |
| WO | WO2009049924 A | 2/2011 |

* cited by examiner

CONSERVATION OF BATTERY LIFE IN GPS ACCESSING PORTABLE DEVICES

CROSS-REFERENCE TO PRIOR APPLICATIONS

This application is the U.S. National Phase application under 35 U.S.C. § 371 of International Application Serial No. PCT/IB2012/057448, filed on Dec. 19, 2012, which claims the benefit of U.S. Application Ser. No. 61/577,737, filed on Dec. 20, 2011. These applications are hereby incorporated by reference herein.

TECHNICAL FIELD OF THE INVENTION

The invention relates to portable or mobile devices that include a receiver, such as a satellite positioning system receiver, the measurements from which are used to provide a measurement of the location of the device.

BACKGROUND TO THE INVENTION

Currently, satellite positioning systems, such as GPS, are one of the most accurate location data sources available to portable or mobile electronic devices. However, there are a number of drawbacks associated with satellite positioning systems. For example, it might not be possible to receive signals from the satellites when the device is indoors, under heavy foliage or in an 'urban canyon' (i.e. between a number of tall buildings), making it impossible to obtain a location measurement (sometimes referred to as a 'fix'). Satellite positioning systems can also be prone to errors in the location measurement which can be due to a number of different reasons, including 'multipathing' where the signals from a satellite can reflect off of buildings before reaching the satellite positioning system receiver. These errors can cause the reported location to be some distance from the actual location, sometimes even as far as several city blocks. Another drawback with satellite positioning systems is that the receiver consumes a relatively large amount of power while making a location measurement.

Although the satellite positioning system receiver can be manually activated and deactivated by a user of the device to help reduce the power consumption, when some event occurs where it is useful to know the exact location of the device (for example if the user of the device is placing an emergency call and needs to provide their exact location, or the user of the device suffers a fall or other accident and the device is configured to automatically request assistance for the user), activating the satellite positioning system receiver and attempting a measurement is not without risk, as it might not be possible to get a measurement in the current location of the device.

Therefore, in such situations, it can be useful to make use of the last known location of the device obtained using the satellite positioning system receiver before the satellite signal was lost. To do this, the satellite positioning system receiver must either collect location measurements continuously (in which the receiver will quickly drain the battery of the device), or a 'breadcrumbing' technique is used, in which the satellite positioning system receiver is selectively activated by the device to intermittently take location measurements. As the receiver is not continuously powered or active, there is some reduction in the power consumption of the device. If the receiver is unable to determine the location of the device when it is activated, the last acquired location measurement (breadcrumb') can be used as an estimate of the current location of the device.

One particular breadcrumbing technique is described in US 2006/0119508. This document describes a method and apparatus for conserving power on a mobile device through motion awareness, in which measurements by an accelerometer and the GPS receiver in the mobile device are used to determine whether the mobile device is in motion. If it is determined that the mobile device is not in motion, the scanning by the GPS receiver can be halted or reduced to a lower duty cycle to conserve power in the mobile device. When it is subsequently determined from the accelerometer data that the mobile device is in motion again, the GPS receiver resumes scanning and measures the current location of the mobile device.

Although this breadcrumbing technique can reduce the power consumption of the device compared to continuous operation of the satellite positioning system receiver, it is desirable to improve the existing breadcrumbing techniques to further reduce the power consumption of a portable or mobile device.

SUMMARY OF THE INVENTION

According to a first aspect of the invention, there is provided a method of controlling a device that comprises a receiver and a movement sensor, the method comprising (a) deactivating the receiver; (b) while the receiver is deactivated, analyzing measurements from the movement sensor to determine a measure of the distance the device has moved from a first location; and (c) in the event that it is determined from the measurements from the movement sensor that the device has moved from the first location by more than a threshold distance, activating the receiver and using the receiver to obtain a second measurement of the location of the device.

In one embodiment, step (b) comprises analyzing the measurements from the movement sensor to determine the total acceleration experienced by the device, and step (c) comprises comparing the total acceleration to a threshold and determining that the device has moved from the first location by more than a threshold distance on expiry of a predetermined time period after determining that the total acceleration exceeds the threshold.

In an alternative embodiment, step (b) comprises analyzing the measurements from the movement sensor to determine the total acceleration experienced by the device, and step (c) comprises comparing the total acceleration to a threshold and determining that the device has moved from the first location by more than a threshold distance if the total acceleration exceeds the threshold for predetermined period of time.

In an alternative, more preferred, embodiment, step (b) comprises analyzing the measurements from the movement sensor to determine the total acceleration experienced by the device at a particular sampling instant and accumulating the determined total acceleration at the particular sampling instant with the total acceleration determined for each preceding sampling instant following the sampling instant at which the first location was determined, and step (c) comprises comparing the accumulated total acceleration to a threshold and determining that the device has moved from the first location by more than a threshold distance if the accumulated total acceleration exceeds the threshold.

In the above embodiments, the step of analyzing the measurements from the movement sensor to determine the total acceleration experienced by the device preferably comprises determining the power of the acceleration.

In alternative preferred embodiments, step (b) comprises analyzing the measurements from the movement sensor using dead-reckoning techniques to determine the distance moved by the device, and step (c) comprises comparing the determined distance to a threshold.

In some of those embodiments, the step of analyzing the measurements from the movement sensor using dead-reckoning techniques to determine the distance moved by the device comprises analyzing the measurements from the movement sensor using step detection algorithms to detect footsteps by a user of the device.

In those dead-reckoning techniques, step (b) preferably comprises using measurements from a plurality of movement sensors to determine the distance moved by the device.

Preferably, the step of analyzing the measurements from the movement sensor comprises using Kalman filter techniques.

Preferably, the movement sensor is an accelerometer that measures the acceleration experienced by the device.

Preferably, the receiver is a satellite positioning system receiver.

In some embodiments, the first location corresponds to the last measurement of the location of the device prior to deactivating the receiver in step (a).

Preferably, after obtaining a second measurement of the location of the device in step (c), the method comprises (d) repeating steps (a), (b) and (c) using the second measurement of the location of the device as the first location.

In some embodiments, step (c) further comprises using the receiver to obtain a measurement of the speed or velocity of the device, and adapting the threshold distance based on the measurement of the speed or velocity of the device.

According to a second aspect of the invention, there is provided a computer program product comprising computer-readable code embodied therein, the code being configured such that, on execution by a suitable computer or processor, the computer or processor performs the method as described above.

According to a third aspect of the invention, there is provided a device, comprising a receiver for obtaining measurements of the location of the device; a movement sensor for measuring the movements of the device; and a processor that is configured to receive measurements from the movement sensor, selectively activate and deactivate the receiver, analyze the measurements from the movement sensor while the receiver is deactivated to determine a measure of the distance the device has moved from a first location, and in the event that it is determined from the measurements from the movement sensor that the device has moved from the first location by more than a threshold distance, activate the receiver such that the receiver obtains a second measurement of the location of the device.

In one embodiment, the processor is configured to analyze the measurements from the movement sensor to determine the total acceleration experienced by the device, compare the total acceleration to a threshold and determine that the device has moved from the first location by more than a threshold distance on expiry of a predetermined time period after determining that the total acceleration exceeds the threshold.

In an alternative embodiment, the processor is configured to analyze the measurements from the movement sensor to determine the total acceleration experienced by the device, compare the total acceleration to a threshold and determine that the device has moved from the first location by more than a threshold distance if the total acceleration exceeds the threshold for predetermined period of time.

In an alternative, more preferred, embodiment, the processor is configured to analyze the measurements from the movement sensor by determining the total acceleration experienced by the device at a particular sampling instant and accumulating the determined total acceleration at the particular sampling instant with the total acceleration determined for each preceding sampling instant following the sampling instant at which the first location was determined; to compare the accumulated total acceleration to a threshold, and to determine that the device has moved from the first location by more than a threshold distance if the accumulated total acceleration exceeds the threshold.

In the above embodiments, the processor is configured to analyze the measurements from the movement sensor to determine the power of the acceleration experienced by the device.

In alternative preferred embodiments, the processor is configured to analyze the measurements from the movement sensor using dead-reckoning techniques to determine the distance moved by the device, and to compare the determined distance to a threshold.

In some of those embodiments, the processor is configured to analyze the measurements from the movement sensor using step detection algorithms to detect footsteps by a user of the device.

In some embodiments, the device comprises a plurality of movement sensors, and the processor is configured to analyze measurements from the plurality of movement sensors to determine the distance moved by the device.

Preferably, the processor is configured to analyze the measurements from the movement sensor using Kalman filter techniques.

Preferably, the movement sensor is an accelerometer that measures the acceleration experienced by the device.

Preferably, the receiver is a satellite positioning system receiver.

In some embodiments, the first location corresponds to the last measurement of the location of the device prior to the deactivation of the receiver by the processor.

Preferably, the processor is configured such that, after obtaining a second measurement of the location of the device using the receiver, the processor deactivates the receiver and analyzes the measurements from the movement sensor while the receiver is deactivated to determine a measure of the distance the device has moved from the location given by the second measurement, and in the event that it is determined from the measurements from the movement sensor that the device has moved from the location given by the second measurement by more than a threshold distance, the processor is configured to activate the receiver such that the receiver obtains a further measurement of the location of the device.

In some embodiments, the receiver is further configured to obtain a measurement of the speed or velocity of the device, and the processor is configured to adapt the threshold distance based on the measurement of the speed or velocity of the device.

BRIEF DESCRIPTION OF THE DRAWINGS

Embodiments of the invention will now be described, by way of example only, with reference to the following drawings, in which.

DETAILED DESCRIPTION OF THE PREFERRED EMBODIMENTS

Although the invention will be described below with reference to a satellite positioning system (e.g. GPS), it will be appreciated that portable or mobile electronic devices can also or alternatively make a location measurement using signals other than those received from a set of satellites, and the breadcrumbing technique according to the invention is applicable to other types of positioning system, such as those that analyze received Wi-Fi network signals and/or analyze Cell IDs of cells in a mobile communication network near to the device.

As described above, the invention relates to a breadcrumbing technique in which a positioning system receiver in a portable or mobile device (such as a satellite positioning system receiver, a Wi-Fi receiver and/or a cellular network signal receiver) is selectively activated and deactivated (i.e. powered and switched off) to intermittently obtain measurements of the location of the device. Conventionally, positioning system receivers (particularly satellite positioning system receivers) are activated according to a schedule, or as soon as motion of the device is detected.

However, according to the invention, measurements from a movement sensor, such as an accelerometer, in a device are collected and processed to determine a measure of the distance that the device has moved from an initial location while the positioning system receiver is deactivated. If the device has moved more than some preset distance from the initial location, the positioning system receiver can be activated in order to obtain a measurement of the current location of the device. Otherwise, the positioning system receiver remains deactivated (unpowered).

Therefore, when the analysis of the measurements from the movement sensor suggests that the device is stationary (in which case there is little need to update the last obtained location measurement), no new measurement of the location of the device will be made by the positioning system receiver. This avoids power being wasted in effectively duplicating measurements of the current location of the device. On the other hand, a new location measurement will be taken whenever the device has moved at least a minimum distance from the location of the last location measurement by the positioning system receiver. Through appropriate selection of the minimum distance, frequent and useful measurements of the location of the device can be made while the device is moving. This means that the device will know that its current location is typically less than the minimum distance from the last location measurement.

Figure 1:
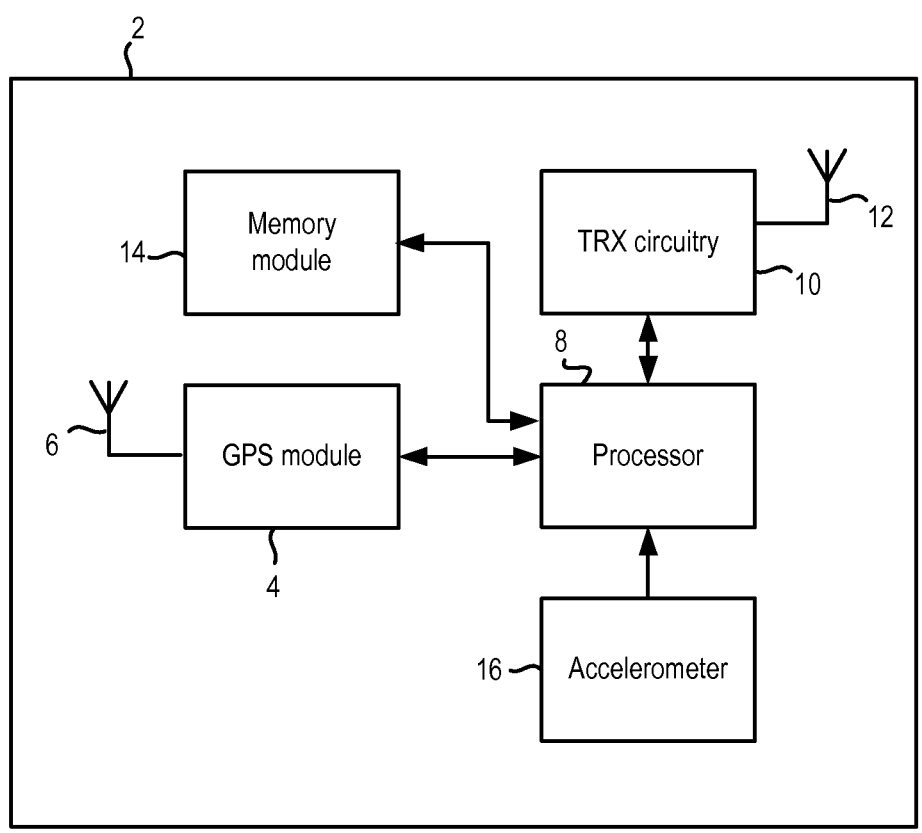
FIG. 1 is a block diagram of a device according to an embodiment of the invention.

An exemplary device according to an embodiment of the invention is shown in FIG. 1. In this embodiment, the device 2 is a mobile telephone or smartphone, although it will be appreciated that in other embodiments the device 2 can take a different form, such as a personal emergency response system (PERS) device, a user-worn fall detector for monitoring whether a user has suffered a fall, or a satellite navigation system for use in a vehicle.

The device 2 comprises a satellite positioning system receiver 4, which in this embodiment is a GPS module 4 (although it will be appreciated that the device 2 can alternatively include receivers for other types of satellite positioning systems or receivers for receiving signals (such as Wi-Fi or cellular signals) from other sources that can be processed to determine the position of the device 2), coupled to an antenna 6 that receives the signals from the GPS satellites. The GPS module 4 is connected to a processor 8 that controls the general operation of the device 2.

As the device 2 in this embodiment is a mobile telephone or smartphone, the device 2 further comprises transceiver circuitry 10 and associated antenna 12 for communicating wirelessly with a mobile communication network.

The device 2 further comprises a memory module 14 that can store at least the last measurement of the location of the device 2 obtained by the GPS module 4 (although preferably a plurality of earlier measurements of the location of the device 2 are stored to allow the change in location of the device 2 over time to be determined). The memory module 14 can also store program code for execution by the processor 8 to perform the processing required to control the device 2 according to the invention.

The device 2 further comprises a movement sensor 16 that measures the movement of the device 2 and that outputs a corresponding signal to the processor 8. The movement sensor 16 is a low-power sensor, in that it consumes significantly less power during operation than a satellite positioning system receiver 4. In a preferred embodiment, the movement sensor 16 is an accelerometer, and the accelerometer 16 preferably outputs a signal indicating the acceleration acting on the device 2 in three-dimensions. In this case, the output of the accelerometer 16 at each sampling instant is provided in the form of a three dimensional vector, $(a_x, a_y, a_z)$. The accelerometer 16 can measure the acceleration with a sampling rate of 30 or 50 Hz, although it will be appreciated that other sampling rates can be used.

Figure 2:
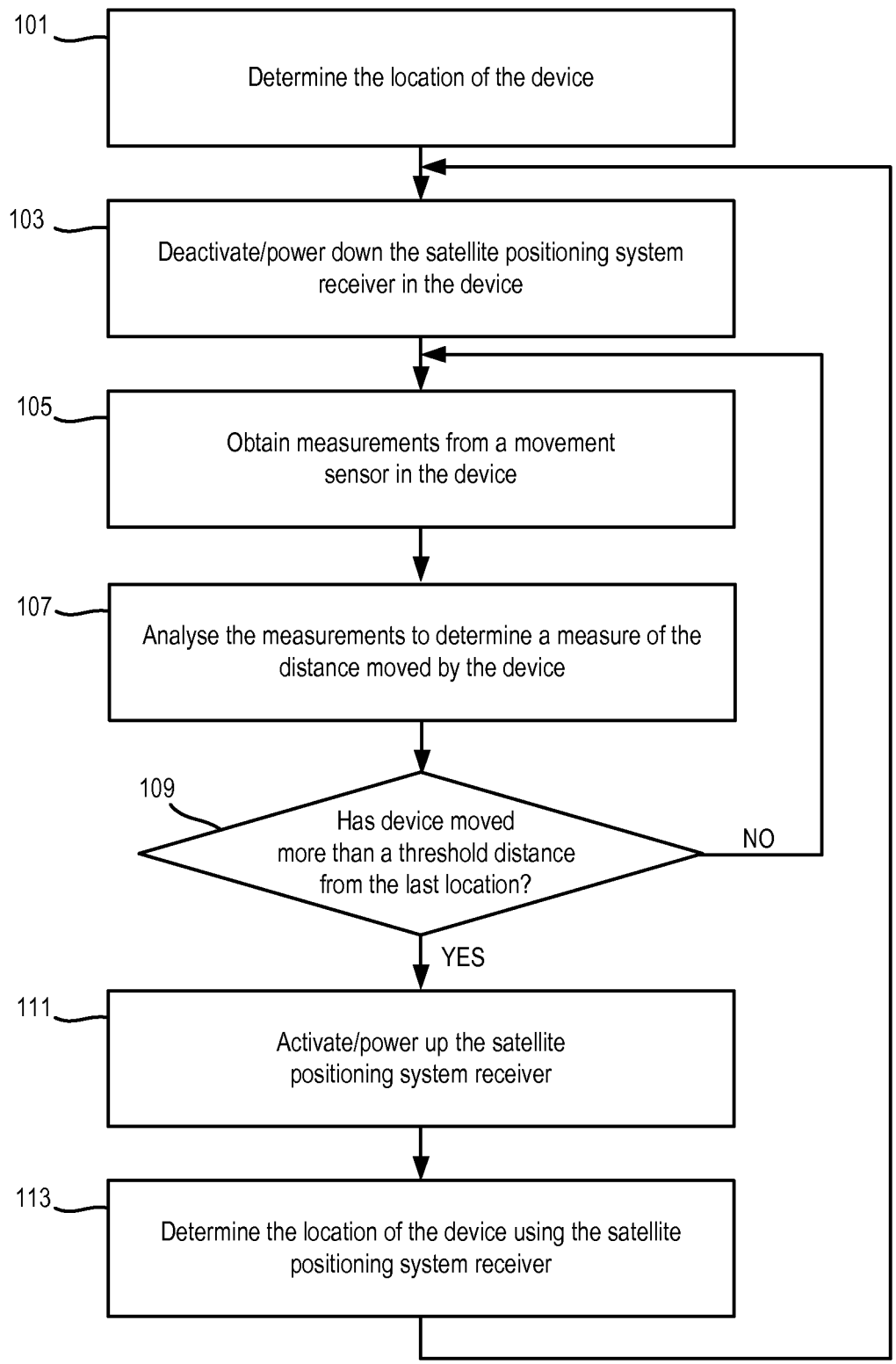
FIG. 2 is a flow chart illustrating a method of operating the device of FIG. 1.

A method of controlling the device 2 in accordance with an embodiment of the invention is shown in FIG. 2.

In step 101, an initial location of the device 2 is determined. This initial location can be stored in the memory module 14, and the initial location used as a reference point to which subsequent movement of the device 2 is compared. This step can comprise obtaining a measurement of the location of the device 2 using the GPS module 4, in which case the exact location of the device 2 will be known. Alternatively, however, if a GPS location measurement is not available (for example because the module 4 is unable to receive the required signals from the satellites), the initial location can be set to a null or zero value.

In step 103, the processor 8 controls the GPS module 4 (or other receiver used to obtain position measurements) to deactivate or power down so that it is no longer collecting or processing measurements from the GPS satellites.

Subsequently, in step 105, measurements of the movement of the device 2 are collected using the movement sensor 16. In particular, measurements of the acceleration acting on the device 2 are collected by accelerometer 16.

In step 107, the measurements of the acceleration acting on the device 2 are provided to the processor 8 which processes the measurements to determine a measure of the distance moved by the device 2 since the initial location was determined in step 101. This processing is performed in substantially real-time, meaning that each measurement from the accelerometer 16 is processed as soon as it is provided to the processor 8, and the distance moved by the device 2 from the initial location up to that sampling instant determined.

After the measure of the distance has been determined, it is determined in step 109 whether the device 2 has moved more than a threshold distance from the location given by the last location measurement (obtained in step 101). If the device 2 has not moved more than the threshold distance, the method returns to step 105 and further measurements of the acceleration acting on the device 2 are collected and analyzed.

If it is determined that the device 2 has moved more than the threshold distance from the location given by the last location measurement, then the processor 8 activates the GPS module 4 (step 111) and the GPS module 4 takes a measurement of the current location of the device 2 (step 113).

After the measurement of the current location of the device 2 is taken, this measurement is stored as the location of the last location measurement, and the method returns to step 103 in which the GPS module 4 is deactivated.

As described further below, determining the measure of the distance moved by the device 2 and therefore whether the device 2 has moved more than a threshold distance from the location given by the last location measurement can be performed in a number of different ways.

In a first implementation, the measure of the distance moved by the device 2 is determined by computing the total amount of acceleration of the device 2 at each sampling instant, comparing the total amount of acceleration at each sampling instant to a threshold and determining that the device 2 has moved a sufficient distance from the location given by the last location measurement when a predetermined period of time expires after the total amount of acceleration at a particular sampling instant exceeds the threshold. That is to say, if the total amount of acceleration at a particular sampling instant exceeds the threshold, then it is assumed that the device 2 has started moving, and waiting for the predetermined period of time to expire allows the device 2 to move a sufficient distance from the location of the last location measurement before activating the GPS module 4 in order to obtain a new location measurement. The use of the timeout period also ensures that there is a minimum time period (equal to the predetermined period of time) between consecutive measurements of the location of the device 2 by the GPS module 4. An exemplary range of values for the predetermined period of time is 30-60 seconds, although it will be appreciated that other values can be used.

The total amount of acceleration can be the power of the acceleration, which can be determined by computing the magnitude of the acceleration signal, with the magnitude given by $$\text{Magnitude} = \sqrt{(a_x^2 + a_y^2 + a_z^2)} \quad (1)$$

and then computing the power of the acceleration due to motion of the device 2 (as opposed to acceleration due to gravity) from the magnitude as $$\text{power} = (\text{Magnitude} - g)^2 \quad (2)$$

where g indicates the magnitude of acceleration due to gravity. The power is then compared to the threshold. It will be appreciated by those skilled in the art that various threshold values can be used.

In a second, more preferred, implementation, the power of the acceleration signal is again computed and compared to a threshold, but in this implementation, the power in the acceleration signal must exceed the threshold for a predetermined period of time before the GPS module 4 can be activated to obtain a new location measurement. By requiring the acceleration power to exceed the threshold for a minimum time period, the effects of sudden, but temporary, movements of the device 2 on the 'breadcrumbing' can be reduced.

In a third, even more preferred, implementation, an accumulator-based algorithm is used to determine whether the device 2 has moved a sufficient distance from the initial location. In this implementation, the power of the acceleration signal is computed as described above, and the computed power at a particular sampling instant is summed with the computed power for all earlier sampling instants following the sampling instant at which the last location measurement was obtained by the GPS module 4. The sum of the computed powers (the 'accumulated power') is compared to a threshold, and when the accumulated power exceeds the threshold, it is determined that the device 2 has moved a sufficient distance from the location of the last location measurement and a new location measurement can be obtained by the GPS module 4. The accumulated power can then be reset to zero. In this implementation, it is assumed that a certain amount of power will be required for the device 2 to move a certain distance (the threshold distance). It will be appreciated by those skilled in the art that various threshold values can be used depending on the sampling rate of the accelerometer 16 and the desired breadcrumbing interval.

In other implementations, it is possible to process the signal from the accelerometer 16 to estimate the actual distance moved by the device 2 since the last location measurement was obtained by the GPS module 4. In these implementations, the signal from the accelerometer 16 is preferably combined with a signal from one or more additional movement/motion sensors, such as a magnetometer and/or a gyroscope, to create a dead-reckoning system in which information from multiple sensors is fused to provide a short-term location estimate. The gyroscope can estimate the orientation of the device 2, and therefore the direction of travel. The magnetometer can indicate the direction of magnetic north, and therefor the direction of travel. Kalman filters can be used in a dead-reckoning system to fuse information from multiple sensors into a short-term location estimate and therefore estimate distances more accurately. The estimated distance can be compared to a threshold to determine if the device 2 has moved a sufficient distance from the location of the last location measurement. The distance threshold can be a distance selected from the range 10-100 meters, although it will be appreciated that values outside this range can be used.

In the above dead-reckoning systems, the accelerometer signal can be processed using step detection algorithms which can detect accelerations consistent with the device 2 being carried by a user that is walking. The device 2 can store a predetermined distance value for a step by the user (for example 0.75 meters) and combine this with the number of steps detected in the accelerometer signal to determine the distance that the device 2 has moved. Again, this distance can be compared to a distance threshold, as described above.

Alternatively, or in addition, information can be derived from the last location measurement obtained by the GPS module 4 and this information used to enhance the accuracy of the measure of the distance moved by the device 2 determined from subsequent acceleration measurements. For example, the GPS module 4 can determine a speed or velocity measurement when it is activated to obtain a new location measurement, and this speed or velocity measurement can be used in combination with subsequent acceleration measurements to determine the measure of the distance moved by the device 2. In particular, the speed measurement determined by the GPS module 4 can be used to alter the threshold values used in the embodiments above. For instance, while driving a car, people experience relatively little acceleration, but move at high speed. In this case, the GPS speed measurement can suggest that the user is in a vehicle, and this can be used to reduce the size of the threshold so that less measured acceleration is required in order to trigger a position measurement. In the case where dead-reckoning is used to determine the measure of the distance moved by the device 2, the GPS speed measurement can be used to calibrate the model of the Kalman filter and improve its accuracy.

There is therefore provided a method of controlling a device to obtain location measurements using a receiver, such as a satellite positioning system receiver, in which the power consumption of the device is reduced compared to conventional 'breadcrumbing' techniques.

While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A method of controlling a device that comprises a satellite positioning system receiver and a movement sensor, the method comprising:
   (a) deactivating the receiver;
   (b) while the receiver is deactivated,
   periodically sampling an accelerometer at a predetermined sampling rate;
   (c) determining a magnitude of the acceleration at each sampling point, wherein the magnitude M of acceleration is defined by $M=(a_x^2+a_y^2+a_z^2)^{1/2}$, where $a_x$, $a_y$, and $a_z$ is the acceleration along each of three orthogonal directions;
   (d) determining a power of the acceleration at each sampling point wherein the power P is defined by: $P=(M-g)2$, where g is acceleration due to gravity; and
   (e) in response to the power of the acceleration exceeding a preselected threshold, activating the receiver to receive signals from the satellite positioning system indicative of an updated current location of the device.

2. The method as claimed in claim 1, wherein, after obtaining the satellite positioning system measurement of the location of the device in step (e), the method comprises:
   (f) repeating steps (a), (b), (c), (d), and (e).

3. The method as claimed in claim 2, wherein step (e) further comprises:
   based on a plurality of the satellite positioning system measurements by the receiver, determining a speed or velocity of the device, and
   adapting the threshold distance based on the determined speed or velocity of the device.

4. A non-transitory computer-readable medium carrying computer code configured to control a device that comprises a satellite positioning system receiver and a movement sensor, where executing the computer code with a computer or processor causes the computer or processor to:
   (a) deactivate the receiver;
   (b) while the receiver is deactivated, periodically sample an accelerometer at a predetermined sampling rate;
   (c) determine a magnitude of the acceleration at each sampling point, wherein the magnitude M of acceleration is defined by $M=(a_x^2+a_y^2+a_z^2)^{1/2}$, where $a_x$, $a_y$, and $a_z$ is the acceleration along each of three orthogonal directions;
   (d) determine a power of the acceleration at each sampling point wherein the power P is defined by: $P=(M-g)2$, where g is acceleration due to gravity; and
   (e) in response to the power of the acceleration exceeding a preselected threshold, activate the receiver to receive signals from the satellite positioning system indicative of an updated current location of the device.

5. The non-transitory computer-readable medium as claimed in claim 4, wherein, after obtaining the satellite positioning system measurement of the location of the device in (e), the executing computer code further causes the computer or processor to repeat (a), (b), (c), (d), and (e).

6. The non-transitory computer-readable medium as claimed in claim 4, wherein the executing computer code further causes the computer or processor to:
   determine a speed or velocity of the device based on a plurality of the satellite positioning system measurements by the receiver; and
   adapt the threshold distance based on the determined speed or velocity of the device.

7. A device comprising:
   a receiver configured to receive signals from a satellite positioning system indicative of current location of the device;
   an accelerometer configured to measure acceleration of the device; and
   a processor configured to:
   (i) after receiving the signals from the satellite positioning system indicative of the current location, deactivate the receiver,
   (ii) after deactivating the receiver, periodically sample the accelerometer at each of a plurality of sampling points,
   (iii) determine a magnitude of the acceleration at each sampling point, wherein the magnitude M of acceleration is defined by $M=(a_x^2+a_y^2+a_z^2)^{1/2}$, where $a_x$, $a_y$, and $a_z$ is the acceleration along each of three orthogonal directions, and
   (iv) determine a power of the acceleration at each sampling point wherein the power P is defined by: $P=(M-g)^2$, where g is acceleration due to gravity, and
   (v) in response to the power of the acceleration exceeding a threshold, activate the receiver to receive signals from the satellite positioning system indicative of an updated current location of the device.

8. The device as claimed in claim 7, wherein the processor is configured to deactivate the receiver and repeat (ii)-(v) after obtaining the updated current location of the device in (v).

9. The device as claimed in claim 8, wherein the processor is configured to calculate a measurement of speed or velocity of the device based on the updated current locations and to adapt the threshold distance based on the speed or velocity of the device.

* * * * *